United States Patent [19]
Farrell et al.

[11] Patent Number: 6,022,892
[45] Date of Patent: Feb. 8, 2000

[54] BIS-PLATINUM COMPLEXES WITH POLYAMINE LIGANDS AS ANTITUMOR AGENTS

[75] Inventors: Nicholas P. Farrell, Richmond, Va.; Ernesto Menta, Cernusco sul Naviglio, Italy; Roberto Di Domenico, Milan, Italy; Silvano Spinelli, Monza, Italy

[73] Assignees: Hoffman-La Roche Inc., Nutley, N.J.; Virginia Commonwealth University, Richmond, Va.

[21] Appl. No.: 09/147,089

[22] PCT Filed: Jul. 22, 1997

[86] PCT No.: PCT/US97/12553

§ 371 Date: Feb. 16, 1999

§ 102(e) Date: Feb. 16, 1999

[87] PCT Pub. No.: WO98/03519

PCT Pub. Date: Jan. 29, 1999

Related U.S. Application Data

[60] Provisional application No. 60/022,306, Jul. 22, 1996.

[51] Int. Cl.[7] .............................. A61K 31/28; C07F 15/00
[52] U.S. Cl. ............................. 514/492; 556/136; 556/137
[58] Field of Search ..................................... 556/136, 137; 514/492

[56] References Cited

U.S. PATENT DOCUMENTS

| | | | |
|---|---|---|---|
| 4,797,393 | 1/1989 | Farrell | 514/188 |
| 4,871,729 | 10/1989 | Farrell | 514/188 |
| 5,107,007 | 4/1992 | Farrell | 556/137 |
| 5,145,848 | 9/1992 | Pasini | 514/185 |
| 5,744,497 | 4/1998 | Valsecchi | 514/492 |

FOREIGN PATENT DOCUMENTS

| | | |
|---|---|---|
| 88/00947 | 2/1988 | WIPO . |
| 91/03482 | 3/1991 | WIPO . |
| 95/26968 | 10/1995 | WIPO . |

*Primary Examiner*—Gary Geist
*Assistant Examiner*—Jean F Vollano
*Attorney, Agent, or Firm*—Nikaido, Marmelstein, Murray & Oram LLP

[57] ABSTRACT

Bis-platinum(II) complexes with polyamine ligands, including spermidine and spermine, are disclosed. The method of making the bis-platinum(II) complexes, using a DMF complex, and the use of the bis-platinum complexes for the treatment of tumors in mammals are also disclosed. The method of making the polyamine ligands and the use of a new polyamine compound as an intermediate in the synthesis of polyamine ligands are also disclosed.

21 Claims, No Drawings

BIS-PLATINUM COMPLEXES WITH POLYAMINE LIGANDS AS ANTITUMOR AGENTS

This application is the nations stage of PCT/US97/12553, filed Jul. 22, 1997 and claims domestic priority of US60/022,306, filed Jul. 22, 1996.

BACKGROUND OF THE INVENTION

The present invention relates to new bis-platinum complexes in which two platinum cores are connected by a polyamine ligand and to pharmaceutical compositions containing them.

The use of platinum complexes in cancer chemotherapy is well known. Cisplatin (CDDP) for example is used in therapy to treat testicular, ovarian, head and neck and small cell lung carcinomas. However, treatment with cisplatin may result in severe nephrotoxicity. A further clinical disadvantage is the problem of acquired drug resistance resulting in the tumor becoming refractory to treatment by the agent.

To overcome the nephrotoxic effects of cisplatin, a second-generation analogue, carboplatin, was developed. Carboplatin, or $[Pt(NH_3)_2(CBDCA)]$ (where CBDCA stands for 1,1'-cyclobutanedicarboxylate), is clinically effective against the same spectrum of carcinomas as cisplatin, but exhibits a reduction in the nephrotoxic effects.

A number of different mono- and bis-platinum complexes have been prepared in an attempt to treat different tumors or carcinomas (U.S. Pat. No. 4,225,529; U.S. Pat. Nos. 4,250,189; 4,553,502; U.S. Pat. No. 4,565,884). None of such compounds is currently used in therapy.

More recently, new bis-platinum(II) complexes are disclosed (U.S. Pat. No. 4,797,393), which have a bridging diamine or polyamine ligand and primary or secondary amines or pyridine type nitrogen-carrying ligands attached to the platinum complex, as well as two different or identical ligands which may be a halide, sulphate, phosphate, nitrate, carboxylate, substituted carboxylate or dicarboxylate. The expert technician will appreciate that the complex is neutral, since two anions counter-balance the +2 charge on each platinum core.

WO 91/03482 further discloses bis-platinum(II) complexes such as those described in U.S. Pat. No. 4,797,393, the main difference consisting in having two nitrogen-carrying neutral ligands and only one charged ligand on each platinum core. This results in a complex having a +2 total charge. These complexes interfere with DNA replication forming interstrand cross-links, which cause conformational changes on the DNA and eventually lead to the inhibition of replication and to the final cytotoxic effect.

Polyamine bridging ligands are generally mentioned as possible ligands in such complexes, but not example is given.

Even if such compounds are able to partially overcome the resistance to cisplatin in cisplatin-resistant cell lines and thus may have a broader spectrum of activity than cisplatin, nevertheless their collateral sensitivity appears lower when compared with cisplatin (see Table I).

On the other hand, polyamines are considered essential in cell proliferation. The naturally occurring polyamines in mammalian cells are putrescine, spermidine and spermine. A wide variety of related amines are found in other organisms and may play critical roles in their physiology. Nevertheless, it is also known that the association of cationic polyamines with negatively charged DNA induces significant structural changes in DNA. Spermidine and spermine can cause DNA to condense and aggregate and induce reversible B-to-Z transition in certain DNA sequences (Marton, L. J. et al., Annu. Rev. Pharmacol. Toxicol., 1995, 35: 55–91). This led the researchers to focus their attention on the potential use of polyamines as antitumor drugs (Basu, H. S. et al., Biochem. J., 1990, 269: 329–334; Yanlong Li et al., J. Med. Chem., 1996, 39: 339–341).

Mono-platinum complexes with spermine are described in J. Clin. Hematol. Oncol., 7(1), 322–9 (1977) and Proc. Int. Congr. Chemother. 13th, 17, 286/100–286/102 (1983), but in both the cases chelates with spermine are obtained. In the first mentioned paper in particular it is described a complex in which the spermine coordinates the whole coordination sphere of the platinum(II) core.

Mono-platinum complexes with polyamines are also disclosed in Can. J. Chem., 72, 1225–9 (1994), but, even if no structure is showed, it can be inferred that they are again chelates.

J. Inorganic Biochem., 53, 177–190 (1994) discloses triplatinum complexes linked by two spermidine molecules. Again the external platinum moieties are involved in a chelating ligand with two spermidine nitrogen atoms.

It can be understood that using polyamines as such in the complex formation it is not possible to avoid that two or more nitrogen atoms be involved in a chelate formation with the platinum coordination sphere.

We have now found that a selected number of bis-platinum(II) complexes of WO 91/03482 having a polyamine bridging ligand are particularly active against both resistant and non-resistant cell lines.

SUMMARY OF THE INVENTION

It is an object of the present invention to provide bis-platinum(II) complexes of formula (I):

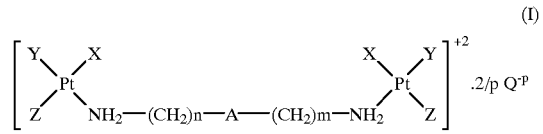

wherein

X, Y and Z ligands are selected in the group consisting of ammonia, chloride, bromide, iodide or carboxylate of formula $R-COO^-$, in which R is a $(C_1-C_4)$alkyl group, with the proviso that two of X, Y and Z are ammonia, the other being selected among chloride, bromide, iodide and carboxylate $R-COO^-$;

n and m, which can be the same or different, are an integer from 2 to 8;

p is the integer 1 or 2;

the bifunctional ligand of formula $H_2N-(CH_2)_n-A-(CH_2)_m-NH_2$ is a polyamine ligand;

$Q^{-p}$ is a suitable counterion, comprising enantiomers and diastereoisomers thereof.

It is a further object of the present invention to provide a process for preparing compounds of formula (I) avoiding the formation of chelates with the platinum coordination sphere.

It is another object of the present invention to provide a method of treating tumors, which are susceptible of platinum-complexes treatment, with one or more compounds of formula (I), as well as pharmaceutical compositions containing compounds of formula (I) with pharmaceutically acceptable eccipients.

It is yet another object of the present invention to provide compounds of formula (VIIc)

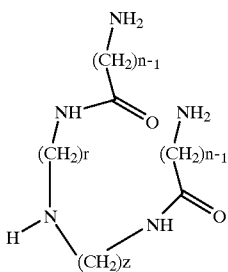

(VIIc)

as intermediates for the synthesis of polyamines.

DETAILED DESCRIPTION OF THE INVENTION

It is an object of the present invention to provide bis-platinum(II) complexes of formula (I):

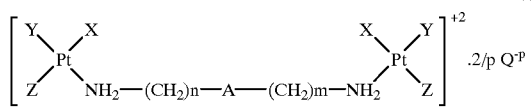

(I)

wherein

X, Y and Z ligands are selected in the group consisting of ammonia, chloride, bromide, iodide or carboxylate of formula R—COO$^-$, in which R is a ($C_1$-$C_4$)alkyl group, with the proviso that two of X, Y and Z are ammonia, the other being selected among chloride, bromide, iodide and carboxylate R—COO$^-$;

n and m, which can be the same or different, are an integer from 2 to 8;

p is the integer 1 or 2;

A is selected in the group consisting of —B—, —B—$(CH_2)_r$—B—, —B—$(CH_2)_r$—B—$(CH_2)_z$—B—, wherein r and z are an integer ranging from 2 to 8 and B is a group —NR$^1$— or —N(R$^2$)$^+$ 1/pQ$^{-p}$, in which R$^1$ is selected in the group consisting of hydrogen, ($C_1$-$C_4$)alkyl, ($C_1$-$C_4$)acyl, tert-butyloxycarbonyl and R$^2$ is selected in the group consisting of hydrogen, ($C_1$-$C_4$)alkyl;

Q$^{-p}$ is an anion selected from chloride, bromide, iodide, nitrate, sulfate, hydrogensulfate, perchlorate.

Enantiomers and diastereoisomers of the compounds of formula (I) are also encompassed in the scope of the present invention.

Preferred compounds of formula (I) are those in which the polyamine connecting ligand of formula $H_2N$—$(CH_2)_n$—A—$(CH_2)_m$—$NH_2$ is spermine or spermidine.

Particularly preferred compounds of formula (I) are those in which the polyamine is spermine or spermidine and two of X, Y and Z ligands are ammonia, the other being a chloride group.

More particularly preferred compounds of formula (I) are those in which, further to the above limitations, the two platinum cores have the ligands in trans configuration.

Particularly preferred salts of the compounds of formula (I) are chloride and nitrate salts.

"Trans configuration" means in the compounds of formula (I) that the two ammonia groups are in trans position, i.e. X and Z are ammonia, the other being as above defined.

The complexes of formula (I) may be prepared according to a procedure which encompasses the following steps:

(a) reaction of a precursor of formula [Pt(X)(Y)(Z)Cl], wherein X, Y and Z are as above defined and wherein the two ammonia groups may be in cis or trans configuration, in dimethylformamide in the presence of equimolar amount of AgNO$_3$, to give the activated intermediate of formula (II):

(II)

(b) condensation of two moles of intermediate (II) with a polyamine of formula (III):

(III)

in which A' has the meanings of A, with the proviso that B cannot be a —NH— or —NH$_2^+$— group, or is a group that can be converted into A by removal of suitable protecting groups, obtaining a Pt complex of formula (I'):

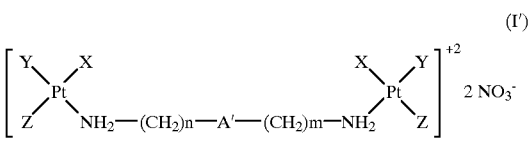

(I')

wherein all the variables are as above defined;

(c) removal of the protecting groups optionally present;

(d) optional neutralization of compounds of formula (I) to give other compounds of formula (I) in which B is a group —NH— or —N($C_1$-$C_4$)alkyl, by treatment with a suitable base in stoichiometric amount, preferentially with a non aqueous organic solution of an hydroxide of an alkaline or alkaline-earth metal;

(e) separation of possibly formed diastereoisomers by conventional chromatographic methods;

The precursors of formula [Pt(X)(Y)(Z)Cl] are known compounds and some of them are commercially available.

The nitrate counterion in the outer coordination sphere can optionally be exchanged with other anions to give other compounds of formula (I).

Step (a) can be performed at temperatures ranging from 0° C. to 50° C., preferentially at room temperature.

Step (b) can be performed at temperatures ranging from −40° C. to room temperature, preferentially −20° C. A 10% to 100% molar excess of platinum intermediates of formula (II) may be used.

Suitable protecting groups which can be used in the present invention are all the protecting groups for a secondary amine. A particularly suitable protecting group is the tert-butyloxycarbonyl group. As stated above, compounds in which B is —N(BOC) group are also encompassed in the scope of the present invention. They can further be converted into other compounds of formula (I) in which B is a —NH$_2^+$— by removal of the BOC group according to step (c).

Step (c) is performed according to conventional methods for the removal of a secondary amine's protecting group. For example, when the tert-butyloxycarbonyl protecting group is used, its removal can be performed by treatment with an organic or inorganic acid, such as treatment with hydrochloric acid in aqueous or in water/methanol solution.

Step (d) can be performed at temperatures ranging from −10° C. to room temperature. Sodium or potassium hydroxide in alcoholic solution may be preferentially employed.

The polyamines of formula (III), in which B is a —N(BOC) group, can be prepared according to the schemes I, II and III.

The process shown in schemes I–III comprises the steps of:

(f) protection of the nitrogen atom of an ω-aminoacid with a suitable protecting group, preferentially a tertbutyloxycarbonyl group, followed by the treatment with a mineral acid, to obtain the free acid;

(g) mono-protection of a diamine with a suitable protecting group, preferentially tert-butyloxycarbonyl group;

(h) reaction of the intermediate obtained in step (f) with that obtained in step (g) to give the intermediate (IV) (scheme I); or alternatively, reaction of the intermediate obtained in step (f) with a diamine to give intermediate (V) (scheme II); or alternatively, reaction of the intermediate obtained in step (f) with the final product of formula (III) reported in scheme (I) (wherein A is a —N(BOC)-group), to give intermediate (VI);

(i) removal of the protecting groups present in intermediates (IV), (V) or (VI), respectively;

(l) reduction of the amide moieties to secondary amines;

(m) protection of the primary amines with suitable protecting groups, preferentially with a trifluoroacetyl group, followed by the protection of the secondary amines with specific protecting groups, preferentially tert-butyloxycarbonyl group;

(n) selective removal of the primary amine's protecting groups, to give compounds of formula (III) in which B is a —N(BOC)-group.

Step (g) can be performed using amounts of protecting reagent ranging from 0.3 to 0.5 moles per mole of diamine. Suitable protecting groups are the protecting groups for a primary amine of an aminoacid, as can be evident to the expert technician, such as those reported in Gree, T. W., Wuts, P.G.M., "Protective Groups in Organic Synthesis", Second Edition, John Wiley & Sons, 1991.

The condensation reaction of step (h) can be performed by activating the carboxylic functionality with methods known to the expert of the art, such as treating it with $SOCl_2$ to give the acyl chloride, or treating the same with N,N'-carbonyldiimidazole; alternatively, the two intermediates can be condensed using a suitable condensing agent, such as dicyclohexylcarbodiimide and the like.

The removal of the protecting groups in step (i) is related to the protecting group which has been used. In particular, when tert-butyloxycarbonyl group is used, then its removal may be performed by treatment with an acid, preferentially trifluoroacetic acid in organic solution.

Step (l) can be performed by using hydrides of alkaline metals, preferentially lithium aluminum hydride. Other reagents which are normally used for the reduction of an amide functionality may be employed as well.

The protecting groups suitable for the protection of a primary and secondary amine according to step (m) are for example those described in Gree, T. W., Wuts, P. G. M., "Protective Groups in Organic Synthesis", Second Edition, John Wiley & Sons, 1991.

The removal of the protecting groups in step (n) is related to the protecting group which has been used. In particular, when a trifluoroacetyl group is used, then its removal may be performed by treating it with an alkaline or alkaline-earth hydroxide in aqueous solution.

As can be seen, scheme II allows to obtain polyamines of formula (III):

$$H_2N-(CH_2)_n-A'-(CH_2)_m-NH_2 \qquad (III)$$

wherein A' is —N(BOC)—$(CH_2)_r$—N(BOC)-group and n and m are the same. It is evident that, when in step (h) of scheme II two different aminoacids are used (i.e. in which n is not the same) instead of two moles of the same aminoacid, then polyamines of formula (III), wherein n and m are different, are obtained. The reaction may be performed in two steps, optionally using a mono-protected diamine in the first step, followed by the selective deprotection of the same and by the condensation of the second aminoacid. Analogously, scheme III allows to obtain polyamines of formula (III) wherein A' is a —N(BOC)—$(CH_2)_r$—N(BOC)—$(CH_2)_z$—N(BOC)-group and n and m are the same.

Polyamines in which n and m are different may be obtained using in step (h) two different aminoacids as above described.

Polyamines of formula (III) in which B is a —N($C_1$–$C_4$) alkyl or —N[($C_1$–$C_4$)alkyl]$^{2+}$ group may be obtained starting from the intermediates obtained in step (m) of scheme I–III, by removal of the secondary amine's BOC protecting groups, followed by treatment with one or two equivalents of an alkylating agent, respectively. A suitable alkylating agent can be an alkyl iodide.

Alternatively, polyamines of formula (III) in which A' is a —N($C_1$–$C_4$)alkyl-$(CH_2)_r$-N($C_1$–$C_4$)alkyl-moiety may be conveniently prepared using a N,N'-(dialkyl)diamine in step (h) (scheme II). In this case, the protection and the deprotection of the secondary amines in steps (m) and (n) respectively are avoided.

The intermediates of formula (VIIa), (VIIb) and (VIIc), which are obtained in step (i), can be easily prepared and converted into polyamines by reduction of the amidic functionality. Therefore, they are advantageous precursor of polyamines.

The compounds of formula (VIIc) are new. A further object of the present invention is therefore to provide compounds of formula (VIIc):

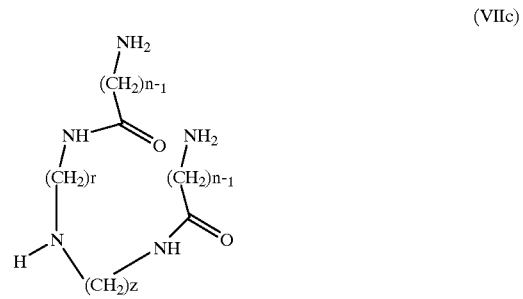

(VIIc)

as intermediates for the synthesis of polyamines having three aza groups inside the chain.

The compounds of formula (I) were tested for their cytotoxic effect "in vitro" on various tumor cell lines, among which murine leukemia L1210, human ovarian carcinoma A2780 and the respective cisplatin resistant sublines L1210/CDDP and A2780/CDDP. Table (I) shows the pharmacological data for some representative compounds of the invention in comparison with cisplatin and with the prior art compound [trans-(PtCl(NH$_3$)$_2$)$_2$ H$_2$N—(CH$_2$)$_6$—NH$_2$] (NO$_3$)$_2$, described in WO 91/03482.

Table I

Cytotoxic activity of cisplatin, the prior art compound

[trans-(PtCl(NH$_3$)$_2$)$_2$ H$_2$N-(CH$_2$)$_6$—NH$_2$] (NO$_3$)$_2$, [trans-(PtCl(NH$_3$)$_2$)$_2$ μ-spermidine]Cl$_3$ and [trans-PtCl(NH$_3$)$_2$)$_2$ μ-spermine]Cl$_4$ against L1210, A2780 and L1210/CDDP, A2780/CDDP cell lines

| compound | example | L1210 IC$_{50}$ 2h$^a$ | A2780 IC$_{50}$ 1h$^d$ | L1210 IC$_{50}$ 72h$^b$ | A2780/CDDP IC$_{50}$ 1h$^a$ | L1210/CDDP IC$_{50}$ 72h$^c$ |
|---|---|---|---|---|---|---|
| trans-(PtCl(NH$_3$)$_2$)$_2$ μ-spermidine|Cl$_3$ | 14 | 0.75 | <0.005 | 0.41 | 0.13 | 0.03 |
| |trans-(PtCl(NH$_3$)$_2$)$_2$ μ-spermine|Cl$_4$ | 16 | 1.0 | <0.005 | 0.6 | 0.4 | 0.6 |
| |trans-(PtCl(NH$_3$)$_2$)$_2$ H$_2$N—(CH$_2$)$_6$—NH$_2$|(NO$_3$)$_2$ | — | 3.7 | 2.3 | 0.43 | 23.8 | 0.1 |
| cisplatin | — | 1.33 | 2.4 | 0.42 | 16.1 | 11.2 | a) IC$_{50}$ (concentration of the drug expressed as (g/ml which causes a 50% inhibition of the cell growth) determined after 2 hours from the drug exposure.

b), c) IC$_{50}$ determined after 72 hours from the drug exposure in the non resistant and in the resistant cell lines, receptively.

d), e) IC$_{50}$ determined after 1 hour from the drug exposure in the non resistant and in the resistant cell lines, receptively.

As can be seen, the compounds of the invention are able to overcome the resistance mechanism which limits the use of cisplatin. This is undoubtedly an important feature of the compounds of the invention.

Even most important, they show, when compared with the prior art compound [trans-(PtCl(NH$_3$)$_2$)$_2$ H$_2$N-(CH$_2$)$_6$—NH$_2$] (NO$_3$)$_2$, a very high activity after 2 hours from the treatment, similar to or even better than that of cisplatin. This feature is a very advantageous one, since it means that the activity can take place quickly, probably due to an increased affinity for the cell and/or the DNA.

In addition, the compounds of the invention were tested in an "in vivo" test in which L1210 and L1210/CDDP tumor cells are inoculated intraperitoneally (ip) in a mouse and the compound is administered ip 24, 120 and 216 hours after tumor inoculation. The compounds evidenced a high antitumor effect in such an experimental model too. For example, [trans-(PtCl(NH$_3$)$_2$)$_2$ (spermine]Cl4 showed a T/C % of 172 at a dose of 2 mg/kg in the L1210CDDP model, versus a T/C % of 110 at a dose of 6 mg/kg of cisplatin. The % T/C was determined using the mean survival time (MST) for each group according to the formula % T/C=[(MST treated)/(MST control)]×100

The compounds of formula (I), when administered to humans and animals bearing tumors which can be treated with cisplatin or two which they are resistant, at doses ranging from 0.1 mg to 1.2 g per square meter of body area, are capable of inducing the regression of said tumors.

More generally, the compounds of the invention can be used for the treatment of the same pathological conditions for which cisplatin is used. This includes the treatment of tumors, sensitization or enhancement of radiations [Douple et al., Cisplatin Current Status and Developments, Ed. A. W. Prestayk et al., Academic Press, 125 (1980); Douple et al., Platinum Metals Res., 29, 118 (1985)] and the treatment of parasitic diseases such as African sleeping sickness [Farrell et al., Biochem. Pharmacol., 33, 961 (1984)].

Therefore, another object of the present invention is a method of treating mammals bearing tumors which can be treated with cisplatin or to which they are resistant with effective antitumor amounts of at least one compound of formula (I).

The effective dosage of the compounds of the invention can be determined by expert clinicians according to conventional methods. The relationship between the dosages used for animals of various species and sizes and those for humans (on the basis of mg/m$^2$ body area) is described by Freirech et al., Quantitative Comparison of Toxicity af Anticancer Agents in Mouse, Rat, Hamster, Dog, Monkey and Man, Cancer Chemother. Rep., 50, N. 4, 219–244 (1966).

Usually, however, the patient will receive doses from 0.1 to 1200 mg/kg body weight of the complex, with a dosage regimen which will vary depending on various factors which are well know to the expert clinicians.

Sometimes it can prove advantageous to administer the platinum complexes of the present invention together with one or more agents which enhance the antitumor activity or relieve the undesirable side effects which may be associated with the platinum complex therapy.

For example, the platinum complexes of the present invention can be administered together with reduced glutathione, as disclosed in GB 2174905 and U.S. Pat. No. 4,871,528.

Moreover, it can be advantageous to administer the platinum complexes of the present invention in combination with other platinum complexes having antitumor activity.

A pharmaceutical composition containing at least one compound of formula (I) in combination with a platinum complex having antitumor activity is a further object of the present invention.

The treatment regimen can suitably be varied, as it is well known to the expert clinician, according to the type of tumor to be treated and the conditions of the patient.

The compounds of the invention are preferably administered as sterile aqueous solutions, optionally containing sodium chloride in suitable concentration (0.1–0.9 mg/ml). The solutions are preferably administered by the intravenous (iv) or intra-arterial (ia) routes, even though other administration forms can be used in particular cases.

The pharmaceutical compositions of the parenteral administration comprise sterile saline solutions, as defined above, or sterile powders for the extemporary preparation of the solutions, as well as oily preparation for intramuscular (im) or intraperitoneal (ip) administrations.

Other useful pharmaceutical compositions can be syrups or similar liquid forms, as well as solid forms such as tablets, capsules and the like, useful for oral administration (os).

The pharmaceutical compositions according to the present invention are prepared following known methods, such as those reported in Remington's Pharmaceutical Sciences Handbook, XVII Ed., Mack Pub., N.Y., U.S.A.

A further object of the present invention are pharmaceutical compositions containing a therapeutically effective amount of at least one compound of formula (I) in admixture with conventional carriers and excipients.

The invention is further illustrated by the following examples.

PREPARATION 1—N-BOC 6-aminohexanoic acid

6-Aminohexanoic acid (10 g) was dissolved into a water solution of potassium carbonate (7.85 g in 80 ml water) at room temperature. A solution of di-tert-butyl dicarbonate (19.4 g) in ethylene glycol dimethyl ether (65 ml) was added at room temperature and the reaction mixture was stirred overnight. Then, after cooling to 0–5° C., 6N hydrochloric acid was dropped into the mixture in order to reach pH=2.

The muddy suspension was extracted with ethyl acetate (2×200 ml). The combined organic extracts were washed with brine (2×50 ml), dried over sodium sulfate and concentrated to a little volume. The oily residue (about 20 g) was dissolved in diiso-propyl ether (20 ml) and diluted with n-hexane (100 ml). After about 1 hour cooling and stirring, a white solid was collected by filtration and dried at room temperature over phosphoric anhydride to yield 14.9 g of the product, m.p. 42–44° C.

PREPARATION 2—N-BOC 1,6-diamino hexane

Under nitrogen atmosphere, a solution of di-tert-butyl dicarbonate (123.6 g) in anhydrous tetrahydrofuran (600 ml) was slowly added over a period of about 3 hours to a cooled (0–5° C.) and stirred solution of 1,6-diamino hexane (200 g) in THF (600 ml). After 3 hours at 10° C. and about 16 hours at room temperature, the solvent was almost completely removed under vacuum. The residual concentrated solution (about 300 ml) was dissolved in tert-butyl methyl ether (460 ml) and washed with 2N sodium hydroxide (300 ml). The aqueous layer was further extracted with tert-butyl methyl ether (2×300 ml). The combined organic extracts were dried over sodium sulfate (50 g) and then concentrated to a little volume and distilled under reduced pressure (0.8 torr, 122–124° C.) to give N-tert-butyloxycarbonyl-1,6-diaminohexane (72 g). The distillation heads contain the excess of hexane diamine which can be recovered for another reaction.

EXAMPLE 1—(N-BOC-6-aminohexyl)-N'-BOC-6-aminocapronamide

Under a nitrogen atmosphere, 1,1'-carbonyl diimidazole (1.7 g) was added portionwise in about 30 minutes to a stirred solution of N-BOC 6-aminohexanoic acid (2 g) in tetrahydrofuran (20 ml) cooled to 0–5° C. At the end of the addition the temperature was brought to 25° C. and stirring was continued for one additional hour. Then a solution of N-BOC-1,6-diamino hexane (1.87 g) in tetrahydrofuran (5 ml) was added to the reaction mixture which was stirred overnight at room temperature. After solvent removal, the residue was dissolved in chloroform (50 ml) and washed with brine, dried over sodium sulfate and concentrated under vacuum. The oily residue (4.5 g) was dissolved in diethyl ether (10 ml) and diluted with n-hexane (50 ml) in order to induce the crystallization. After 1 hour stirring at room temperature, a white solid was collected by filtration, affording, after drying, 3.5 g of the product, m.p. 83–85° C.

EXAMPLE 2—(N-BOC-6-aminohexyl) 6-aminocapronamide (structure VIIa)

A solution of (N-BOC-6-aminohexyl)-N'-BOC-6-aminocapronamide (5.3 g) in methylene chloride (50 ml) and trifluoroacetic acid (9.5 ml) was stirred overnight at room temperature. The reaction mixture was cautiously added to cool 6N sodium hydroxide (100 ml), the chlorinated solvent was separated and the aqueous layer was further extracted with methylene chloride (6+50 ml). The combined organic extracts were dried over sodium sulfate and concentrated under vacuum to yield 2.34 g of the product as a colorless oil which tends to become solid upon standing.

EXAMPLE 3—N-(6-aminohexyl)hexanediamine

To a suspension of 0.1 g of lithium aluminum hydride in 10 ml of anhydrous tetrahydrofuran, under stirring and under nitrogen atmosphere, 2.9 g of N-(6-aminohexyl) 6-aminocapronamide are added portionwise. At the end of the addition the reaction mixture is heated at reflux for about 24 hours, then it is cooled to 5° C. and added cautiously firstly with water, then with 15% sodium hydroxide and again with water, in order to destroy the lithium aluminum hydride excess. After an additional hour under stirring, the mixture is filtered through celite and the filtrate is dried over sodium sulfate. The solvent is evaporated off under reduced pressure to give 2.2 g of the product.

EXAMPLE 4

According to the procedures described in the preparations 1 and 2 and in the examples 1–3, the following polyamines were obtained:

N-(7-aminoheptyl)octanediamine;

N-(3-aminopropyl)butanediamine (spermidine);

N-(2-aminoethyl)ethanediamine;

N-(2-aminoethyl)pentanediamine;

N-(4-aminobutyl)hexanediamine.

EXAMPLE 5—$N^4$-(tertbutyloxycarbonyl)-$N^1$,$N^8$-(bistrifluoroacetyl)spermidine To a solution of commercial N-(3-aminopropyl) butanediamine (spermidine; 4 g) in acetonitrile (60 ml), ethyl trifluoroacetate (11.4 ml) and water (0.6 ml) were added and the reaction mixture was heated at reflux for 3 hours. The solvent was partially removed under vacuum to reach a final volume of about 20 ml. The crystallization of a white solid occurred and, after the addition of methylene chloride (5 ml), the precipitate was filtered off and washed with methylene chloride. 10.87 g of $N^1$,$N^8$-(bistrifluoroacetyl)spermidine trifluoroacetate as a white solid (m.p. 144–146° C.) were collected.

A suspension of 10 g of $N^1$,$N^8$-(bistrifluoroacetyl) spermidine trifluoroacetate in 67 ml of triethylamine, kept under nitrogen atmosphere, was cooled to 0° C. and a solution of di-tert-butyl dicarbonate (5.3 g) in 10 ml of tetrahydrofuran was added. After the addition, a clear yellow solution was obtained with the presence of a little gummy white solid at the bottom of the flask and the mixture was allowed to come to room temperature. About 3 hours later the yellow solution was quenched in water (200 ml) and extracted with ethyl acetate (3×100 ml). The combined organic extracts were washed with water and dried over sodium sulfate. The solvent was removed under vacuum and the residual oil (10 g) was crystallized from diethyl ether-:hexane 1:3 (40 ml) to yield 9.5 g of the product as a white solid, m.p. 73–75° C.

EXAMPLE 6—$N^4$-(tertbutyloxycarbonyl) spermidine

To a solution of 2 g of $N^4$-(tertbutyloxycarbonyl)-$N^1$,$N^8$-(bistrifluoroacetyl)spermidine in 60 ml of methanol, cooled at 10° C., 50 ml of 0.2N sodium hydroxide were added dropwise and the mixture was allowed to come to room temperature and it was stirred overnight. After methanol removal under vacuum, the aqueous suspension was extracted with a mixture of chloroform:methanol 9:1 (5×20 ml). The combined organic extracts were dried over sodium sulfate and concentrated to dryness affording 1 g of the product as a yellow oil.

EXAMPLE 7—$N^1,N^{12}$-(bistrifluoroacetyl)spermine bis-trifluoroacetate

To a solution of spermine (3.2 g) in acetonitrile (50 ml), ethyl trifluoroacetate (9.4 ml) and water (0.64 ml) were added and the reaction mixture was heated at reflux for 3 hours. Then the reaction mixture was allowed to come to room temperature and 15 ml of methylene chloride were added. The crystallization of a white solid occurred and the precipitate was filtered off and washed with methylene chloride. 8.67 f of the product as a white solid (m.p. 203–206° C.) were collected.

EXAMPLE 8—$N^1,N^{12}$-(bistrifluoroacetyl)-$N^4,N^9$-(bis-tertbutyloxycarbonyl)spermine A suspension of the product of example 7 (8.67 g) in 43 ml of triethylamine, kept under nitrogen atmosphere, was cooled to 0° C. and a solution of di-tertbutyl dicarbonate (6.25 g) in 15 ml of tetrahydrofuran was added. About 3 hours later the yellow solution was quenched in water (150 ml) and extracted with ethyl acetate (3×50 ml). the combined organic extracts were washed with water and dried over sodium sulfate. The solvent was removed under vacuum and the residual oil (9 g) was crystallized from diethyl ether (45 ml) to yield 7.6 g of the product as a white solid, m.p. 104–106° C.

EXAMPLE 9—$N^4,N^9$-(bis-tertbutyloxycarbonyl) spermine

To a solution of $N^1,N^{12}$-(bistrifluoroacetyl)-$N^4,N^9$-(bis-tertbutyloxycarbonyl)spermine (3.3 g) in methanol (105 ml), cooled at 10° C., 60 ml of 0.2N sodium hydroxide were added dropwise and the mixture was allowed to come to room temperature and stirred overnight. After the removal of methanol under vacuum, the aqueous suspension was extracted with a mixture of chloroform:methanol 9:1 (6×50 ml). The combined organic extracts were dried over sodium sulfate and concentrated to dryness affording 1.33 g of the product as a pale yellow oil.

EXAMPLE 10

Repeating the procedures of examples 5 and 6 on the polyamines of examples 3 and 4, the following intermediates are obtained:

N-(6-aminohexyl)-N-(tertbutyloxycarbonyl) hexanediamine

N-(7-aminoheptyl)-N-(tertbutyloxycarbonyl) octanediamine;

N-(2-aminoethyl)-N-(tertbutyloxycarbonyl) ethanediamine;

N-(2-aminoethyl)-N-(tertbutyloxycarbonyl) pentanediamine;

N-(4-aminobutyl)-N-(tertbutyloxycarbonyl) hexanediamine.

EXAMPLE 11—Compounds of formula (VIIb) and (VIIc)

According to the procedures of preparation 1 and of the examples 1 and 2, by using the suitable not protected diamines or alternatively the compounds of examples 6 and 9, the following compounds are obtained:

N,N'-(bis-(6-aminohexanoyl))hexanediamine;
N,N'-(bis-(7-aminoheptanoyl))octanediamine;
N,N'-(bis-(2-aminoacetyl))ethanediamine;
N,N'-(bis-(2-aminoacetyl))pentanediamine;
N,N'-(bis-(4-aminobutanoyl))hexanediamine;
N,N'-(bis-(3-aminopropanoyl))butanediamine;
N,N'-(bis-(8-aminooctanoyl))octanediamine;
N,N'-(bis-(5-aminopentanoyl))heptanediamine;
$N^1N^{13}$-(bis-(6-aminohexanoyl)-1,13-diamino-7-azatridecane;
$N^1N^{16}$-(bis-(2-aminoacetyl)-1,16-diamino-8-azahexadecane;
$N^1N^5$-(bis-(4-aminobutanoyl)-1,5-diamino-3-azapentane;
$N^1N^8$-(bis-(3-aminopropanoyl)-1,8-diamino-3-azaoctane;
$N^1N^{11}$-(bis-(2-aminoacetyl)-1,11-diamino-5-azaundecane;
$N^1N^{13}$-(bis-(4-aminobutanoyl)-1,13-diamino-7-azatridecane;
$N^1N^{16}$-(bis-(5-aminopentanoyl)-1,16-diamino-8-azahexadecane;
$N^1N^5$-(bis-(7-aminoheptanoyl)-1,5-diamino-3-azapentane;
$N^1N^8$-(bis-(6-aminohexanoyl)-1,8-diamino-3-azaoctane;
$N^1N^{11}$-(bis-(8-aminooctanoyl)-1,11-diamino-5-azaundecane;
$N^1N^{17}$-(bis-(8-aminooctanoyl)-1,17-diamino-9-azaheptadecane;

EXAMPLE 12

Repeating the procedures described in examples 3 and 7–9, starting from the intermediates of example 11, the following protected polyamines are obtained:

$N^7,N^{14}$-(bis-tertbutyloxycarbonyl)-1,20-diamino-7,14-diazaicosane;
$N^8,N^{17}$-(bis-tertbutyloxycarbonyl)-1,25-diamino-8,17-diazapentacosane;
$N^3,N^6$-(bis-tertbutyloxycarbonyl)-1,8-diamino-3,6-diazaoctane;
$N^3,N^9$-(bis-tertbutyloxycarbonyl)-1,11-diamino-3,9-diazaundeane;
$N^5,N^{12}$-(bis-tertbutyloxycarbonyl)-1,16-diamino-5,12-diazahexadecane;
$N^4,N^9$-(bis-tertbutyloxycarbonyl)-1,12-diamino-4,9-diazadodecane;
$N^9,N^{18}$-(bis-tertbutyloxycarbonyl)-1,26-diamino-9,18-diazahexacosane;
$N^6,N^{14}$-(bis-tertbutyloxycarbonyl)-1,19-diamino-6,14-diazanonadecane;
$N^7,N^{14},N^{21}$-(tris-tertbutyloxycarbonyl)-1,27-diamino-7,14,21-triazaheptacosane;
$N^3,N^{11},N^{20}$-(tris-tertbutyloxycarbonyl)-1,22-diamino-3,11,20-triazadocosane;
$N^5,N^8,N^{11}$-(tris-tertbutyloxycarbonyl)-1,15-diamino-5,8,11-triazapentadecane;
$N^4,N^7,N^{13}$-(tris-tertbutyloxycarbonyl)-1,16-diamino-4,7,13-triazahexadecane;
$N^3,N^8,N^{15}$-(tris-tertbutyloxycarbonyl)-1,17-diamino-3,8,15-triazaheptadecane;

$N^5,N^{12},N^{19}$-(tris-tertbutyloxycarbonyl)-1,23-diamino-5,12,19-triazatricosane;

$N^6,N^{14},N^{23}$-(tris-tertbutyloxycarbonyl)-1,28-diamino-6,14,23-triazaoctacosane;

$N^8,N^{11},N^{14}$-(tris-tertbutyloxycarbonyl)-1,21-diamino-8,11,14-triazahenicosane;

$N^7,N^{10},N^{16}$-(tris-tertbutyloxycarbonyl)-1,22-diamino-7,10,16-triazadocosane;

$N^9,N^{14},N^{21}$-(tris-tertbutyloxycarbonyl)-1,29-diamino-9,14,21-triazanonacosane;

$N^9,N^{27},N^{27}$-(tris-tertbutyloxycarbonyl)-1,35-diamino-9,18,27-triazatetratriacontane;

EXAMPLE 13—[trans-(PtCl(NH$_3$)$_2$)$_2$(—N—BOC-spermidine]NO$_3$.Cl

A suspension of [trans-PtCl$_2$(NH$_3$)$_2$] (TDDP; 1.64 g) and silver nitrate (0.9 g) in 120 ml of dimethyl formamide was stirred at room temperature for 18 hours, then the precipitated silver chloride was filtered off. The filtrate was cooled to $-20°$ C. and a solution of 0.65 g of $N^4$-(tertbutyloxycarbonyl) spermidine in 28.8 ml of dimethyl formamide was added dropwise within 10 minutes. The reaction mixture was stirred 3 hours at $-20°$ C. and an additional hour at room temperature, then it was evaporated to dryness. The residue was stirred in 100 ml of a mixture of acetone:diethyl ether 1:1 for 8 hours and a yellowish solid was filtered off (about 1.8 g). said solid was stirred in 250 ml of methanol for 6 hours and the unreacted TDDP was filtered off. To the yellow filtrate 80 mg of sodium chloride were added, then the mixture was stirred for 1 hour and concentrated to about 80 ml. The solution was kept at $-18°$ C. overnight, until a white solid separated, which was filtered and washed with acetone:diethyl ether 1:1. The solid was recrystallized from 75 ml of methanol to give 0.4 g of the product.

$^1$H-N.M.R. (200 MHz) in D$_2$O 1.32 ppm (s, 9H); 1.5 ppm (m, 4H); 1.8 ppm (br. 2H); 2.55 ppm (m, 4H); 3.15 ppm (m, 4H); 3.73 ppm (br, 4H).

Elem. anal. % calcd/found: C 16.53/16.72; H 4.52/4.52; N 12.85/12.61; Cl 12.20/12.77; Pt 44.74/44.59.

EXAMPLE 14—[trans-(PtCl(NH$_3$)$_2$)$_2$-(-spermidine]Cl$_3$

A suspension of 0.56 g of [trans-(PtCl(NH$_3$)$_2$)$_2$ (—N—BOC-spermidine].NO$_3$.Cl in 50 ml of methanol was treated with 13 ml of conc. hydrochloric acid and 13 ml of water. The reaction mixture was stirred for 3 hours at room temperature, until a white solid precipitated, which was filtered off, washed twice with 20 ml of acetone and once with 20 ml of diethyl ether. The solid was then stirred in 80 ml of diethyl ether:acetone 1:1 overnight and separated by filtration, obtaining 0.34 g of the product.

$^1$H-N.M.R. (200 MHz) in D$_2$O 1.62 ppm (m, 4H); 1.98 ppm (m, 2H); 2.63 ppm (m, 4H); 2.95 ppm (m, 4H); 3.7 ppm (br, 4H).

Elem. anal. % calcd/found: C 10.75/10.69; H 4.13/4.23; N 12.54/12.24; Cl 22.67/22.38; Pt 49.91/48.81.

EXAMPLE 15—[trans-(PtCl(NH$_3$)$_2$)$_2$ (—N,N'-bis-BOC-spermine]-NO$_3$.Cl

Following the procedure of example 13 the title compound was prepared. The crude product was precipitated by the reaction mixture by adding first 100 ml of acetone, followed by 100 ml of diethyl ether. The resulting solid was separated and stirred in 100 ml of methanol containing 220 mg of sodium chloride for 4 hours. The solution was kept at $-18°$ C. for 2 hours, then a white solid separated (0.87 g). The solid was dissolved in 100 ml of methanol and 0.5 g of charcoal were added. After stirring for 30 minutes, the mixture was filtered, concentrated to about 10 ml and kept at $-18°$ C. overnight, giving 600 mg of the product as a white solid.

EXAMPLE 16—[trans-(PtCl(NH$_3$)$_2$)$_2$ (-spermine]Cl$_4$

A solution containing 0.39 g of [trans-(PtCl(NH$_3$)$_2$)$_2$ (—N,N'-bis-BOC-spermine]-NO$_3$Cl and 10 ml of conc. hydrochloric acid in 25 ml of methanol and 10 ml of water was stirred at room temperature for 4 hours, during which a white solid precipitated. The mixture was kept at $-18°$ C. for 1 hour, then filtered, the solid was washed with acetone and diethyl ether (20 ml each) and dried, yielding 0.28 g of the product.

$^1$H-N.M.R. (200 MHz) in D$_2$O 1.65 ppm (m, 4H); 1.97 ppm (m, 4H); 2.66 ppm (m, 4H); 2.97 ppm (m, 8H).

Elem. anal. % calcd/found: C 13.72/13.11; H 4.61/4.46; N 12.80/12.34; Cl 24.30/24.22; Pt 44.57/44.71.

EXAMPLE 17

According to the procedures described in examples 13 and 14, starting from cis- or trans-platin and the suitable N-BOC polyamines, the following platinum complexes were prepared:

cis-[(PtCl(NH$_3$)$_2$)$_2$ $\mu$-spermidine]CL$_3$;

[trans-(PtCl(NH$_3$)$_2$)$_2$ (N-(6-aminohexyl)-hexanediamine)]Cl$_3$ $^1$H-N.M.R. in D$_2$O 3.0 ppm (t, 4H); 2.65 ppm (brt, 4H); 1.7 ppm (brs, 8H); 1.35 ppm (m, 8H);

Elem. anal. % calcd/found: C 16.92/16.88; H 4.97/5.09; N 11.51/11.26; Cl 20.81/19.66; Pt 45.80/45.04.

[trans-(PtCl(NH$_3$)$_2$)$_2$ (N-(7-aminoheptyl)-octanediamine)]Cl$_3$;

$^1$H-N.M.R. in D$_2$O 3.0 ppm (t, 4H); 2.7 ppm (brt, 4H); 1.7 ppm (m, 8H); 1.35 ppm (brs, 14H) $^{195}$Pt-NMR in D$_2$O: $-2422$ ppm;

Elem. anal. % calcd/found: C 20.15/20.37; H 5.41/5.42; N 10.97/10.67; Cl 19.83/19.66; Pt 43.64/42.96.

[trans-(PtCl(NH$_3$)$_2$)$_2$ (N-(2-aminoethyl)-ethanediamine)]Cl$_3$;

[cis-(PtCl(NH$_3$)$_2$)$_2$ (N-(2-aminoethyl)-pentanediamine)]Cl$_3$;

[cis-(PtCl(NH$_3$)$_2$)$_2$ (N-(4-aminoethyl)-hexanediamine)]Cl$_3$;

[cis-(PtCl(NH$_3$)$_2$)$_2$ $\mu$-spermine]Cl$_4$, 1H N.M.R. in D2O: 1.73 ppm (m, 4H); 2.13 ppm (m, 4H); 2.75 ppm (m, 4H); 3.13 ppm (m, 8H), elem. anal. % calcd/found: C 13.72/13.68; H 4.61/4.71; N 12.80/12.56; Cl 24.30/23.98; Pt 44.57/44.57;

[trans-(PtCl(NH$_3$)$_2$)$_2$ (1,20-diamino-7,14-diazaicosane)]Cl$_4$;

[trans-(PtCl(NH$_3$)$_2$)$_2$ (1,25-diamino-8,17-diazapentacosane)]Cl$_4$;

[trans-(PtCl(NH$_3$)$_2$)$_2$ (1,8-diamino-3,6-diazaoctane)]Cl$_4$;

[trans-(PtCl(NH$_3$)$_2$)$_2$ (1,11-diamino-3,9-diazaundecane)]Cl$_4$;

[cis-(PtCl(NH$_3$)$_2$)$_2$ (1,16-diamino-5,12-diazahexadecane)]Cl$_4$;

[trans-(PtCl(NH$_3$)$_2$)$_2$ (1,12-diamino-4,9-diazadodecane)]Cl$_4$;

[trans-(PtCl(NH$_3$)$_2$)$_2$ (1,26-diamino-9,18-diazahexacosane)]Cl$_4$;

[cis-(PtCl(NH$_3$)$_2$)$_2$ (1,19-diamino-6,14-diazanonadecane)]Cl$_4$;

[trans-(PtCl(NH$_3$)$_2$)$_2$ (1,27-diamino-7,14,21-triazaheptacosane)]Cl$_5$;

[trans-(PtCl(NH$_3$)$_2$)$_2$ (1,22-diamino-3,11,20-triazadocosane)]Cl$_5$;

[trans-(PtCl(NH$_3$)$_2$)$_2$ (1,15-diamino-5,8,11-triazapentadecane)]Cl$_5$;

[trans-(PtCl(NH$_3$)$_2$)$_2$ (1,16-diamino-4,7,13-triazahexadecane)]Cl$_5$;

[trans-(PtCl(NH$_3$)$_2$)$_2$ (1,17-diamino-3,8,15-triazaheptadecane)]Cl$_5$;

[cis-(PtCl(NH$_3$)$_2$)$_2$ (1,23-diamino-5,12,19-triazatricosane)]Cl$_5$;

[trans-(PtCl(NH$_3$)$_2$)$_2$ (1,28-diamino-6,14,23-triazaoctacosane)]Cl$_5$;

[trans-(PtCl(NH$_3$)$_2$)$_2$ (1,21-diamino-8,11,14-triazahenicosane)]Cl$_5$;

[cis-(PtCl(NH$_3$)$_2$)$_2$ (1,22-diamino-7,10,16-triazadocosane)]Cl$_5$;

[trans-(PtCl(NH$_3$)$_2$)$_2$ (1,29-diamino-9,14,21-trizanonacosane)]CL$_5$;

[cis-(PtCl(NH$_3$)$_2$)$_2$ (1,35-diamino-9,18,27-trizanonacosane)]CL$_5$;

New compound—[trans-(PtCl(NH$_{3)2)2}$(1,16-diamino-7,10-diazahexadecane)].4NO$_3^-$ $^1$H-NMR in D$_2$O 3.1 ppm (t, 8H); 2.7 ppm (m, 4H); 1.57 ppm (m, 12H); 1.45 ppm (dt, 4H)

$^{195}$Pt-NMR in D$_2$O: −2424 ppm;

Elem. anal. % calcd/found: C 16.20/16.49; H 4.66/4.81; N 16.20/15.68; Cl 6.83/7.22; Pt 37.60/36.93.

[trans-(PtCl(NH$_{3)2)2}$(1,16-diamino-6,11-diazahexadecane)].4NO$_3^-$ $^1$H-NMR in D$_2$O 3.45 ppm (brs, 4H); 3.15 ppm (t, 4H); 2.7 ppm (brs, 4H); 1.75 ppm (brs, 8H); 1.45 ppm (brs, 8H)

$^{195}$Pt-NMR in D$_2$O: −2433 ppm;

Elem. anal. % calcd/found: C 16.20/16.30; H 4.66/4.88; N 16.20/15.94; Cl 6.83/6.58; Pt 37.60/36.28.

EXAMPLE 18

According to the procedure described in example 13, starting from the suitable polyamine derivatives, the following bis-platinum complexes are obtained:

[trans-(PtCl(NH$_{3)2)2}$(1,13-diamino-N$^7$-tert-butoxycarbonyl-7-azatridecane)]dinitrate, $^1$H-NMR in DMSO: 3.1 ppm (brt, 4H); 2.5 ppm (m, 4H); 1.15–1.6 ppm (m+s, 16-9H)

Elem. anal. % calcd/found: C 21.08/20.60; H 5.10/5.13; N 13.01/12.98; Cl 7.32/7.59; Pt 40.28/41.03;

[trans-(PtCl(NH$_{3)2)2}$(N$^4$,N$^9$-bis(tert-butoxycarbonyl)-N$^1$,N$^{12}$-spermine)]dinitrate, $^1$H-NMR in DMSO: 3.1 ppm (brs, 8H); 2.5 ppm (brm, 4H); 1.7 ppm (m, 4H); 1.4 ppm (brs, 22H), $^{195}$Pt-NMR in DMSO: −2424 ppm;

Elem. anal. % calcd/found: C 22.75/22.63; H 5.16/5.12; N 13.27/12.97; Cl 6.72/6.47; Pt 36.96/36.11;

[trans-(PtCl(NH$_{3)2)2}$(1,16-diamino-N$^6$,N$^{11}$-bis(tert-butoxycarbonyl)-6,11-diazahexadecane)]dinitrate, $^1$H-NMR in MeOD: 3.8 ppm (m, 8H); 2.7 ppm (m, 4H); 1.3–1.8 ppm (m, 34H);

$^{195}$Pt-NMR in MeOD: −2433 ppm;

Elem. anal. % calcd/found: C 25.92/26.96; H 5.62/5.91; N 12.60/12.43; Cl 6.38/5.96; Pt 35.09/34.12;

[trans-(PtCl(NH$_{3)2)2}$(1,16-diamino-N$^7$,N$^{10}$-bis(tert-butoxycarbonyl)-7,10-diazahexadecane)]dinitrate, $^1$H-NMR in MeOD: 3.35 ppm (brs, 4H); 3.2 ppm (t, 4H); 2.7 ppm (m, 4H); 1.45 ppm (m, 34H), $^{195}$Pt-NMR in MeOD: −2435 ppm;

Elem. anal. % calcd/found: C 25.92/26.57; H 5.62/5.76; N 12.60/12.45; Cl 6.38/6.10; Pt 35.09/34.64;

[trans-(PtCl(NH$_{3)2)2}$(1,16-diamino-N$^8$,N$^8$-dimethyl-8-azahexadecane)]nitrate dichloride, $^1$H-NMR in D$_2$O/DCl: 3.2 ppm (m, 4H); 3.0 ppm (s, 6H); 2.6 ppm (m, 4H); 1.6 ppm (m, 8H); 1.3 ppm (brs, 14H), $^{195}$Pt-NMR in D$_2$O: −2419 ppm;

Elem. anal. % calcd/found: C 21.52/21.66; H 5.53/5.81; N 11.81/10.18; Cl 14.95/13.59; Pt 41.13/40.75;

[trans-(PtCl(NH$_{3)2)2}$(1,13-diamino-N$^7$,N$^7$-dimethyl-7-azatridecane)]trinitrate, $^1$H-NMR in D$_2$O: 3.0 ppm (s, 6H); 3.35 ppm (m, 4H); 2.5–2.7 ppm (m, 4H); 1.75 ppm (m, 8H); 1.4 ppm (m, 8H), $^{195}$Pt-NMR in D$_2$O: −2420 ppm;

Elem. anal. % calcd/found: C 17.52/17.88; H 4.83/4.93; N 14.59/14.37; Cl 7.39/7.25; Pt 40.66/40.12;

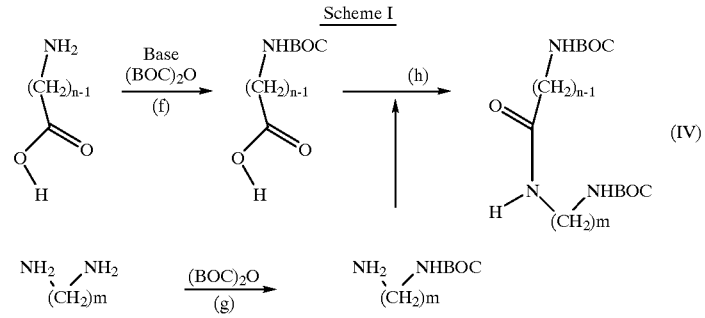

Scheme I

-continued
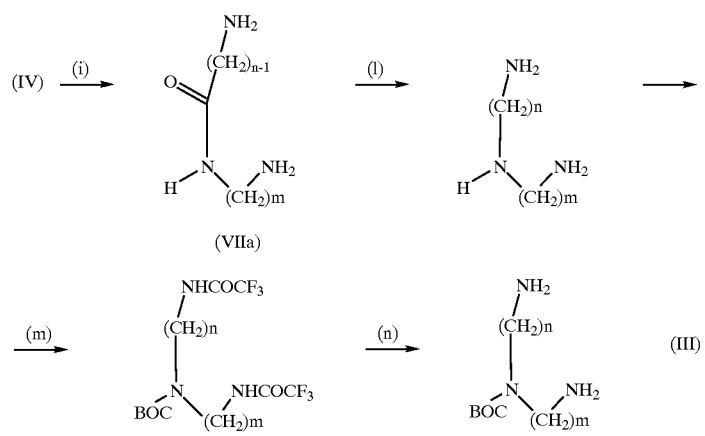
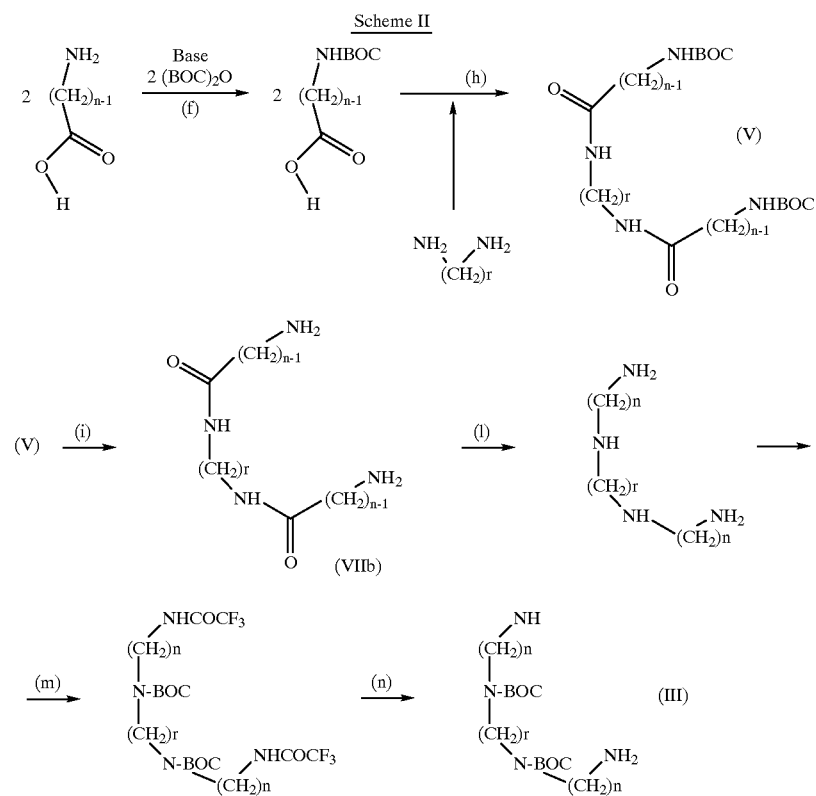

Scheme III
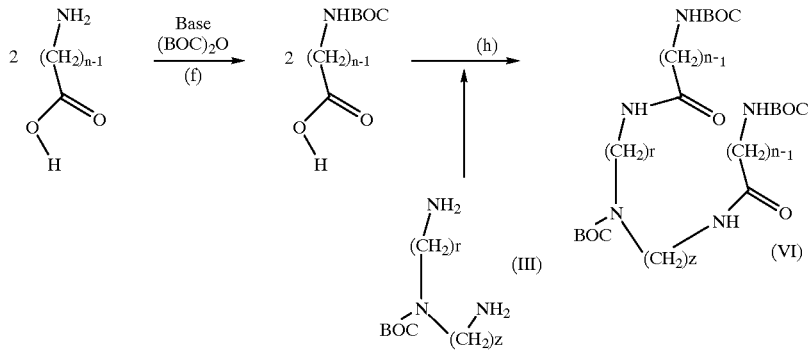
Scheme III
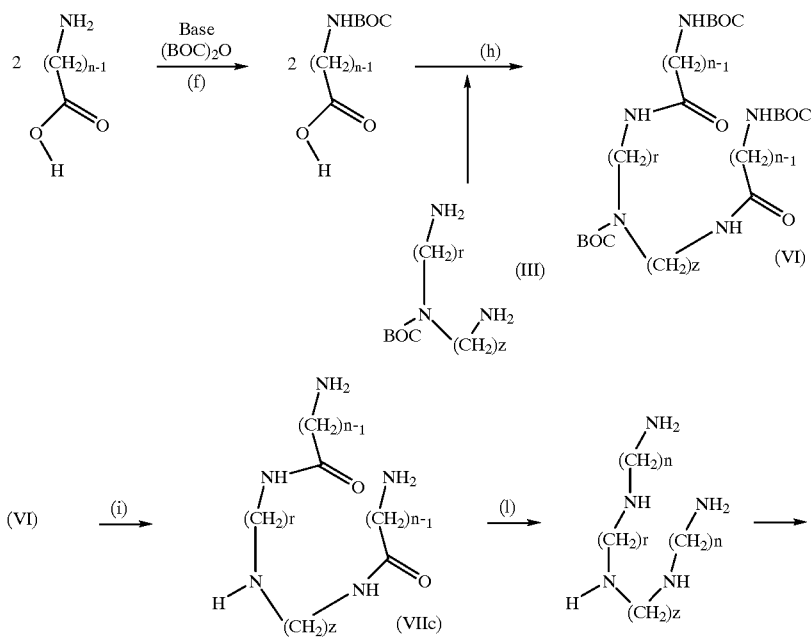
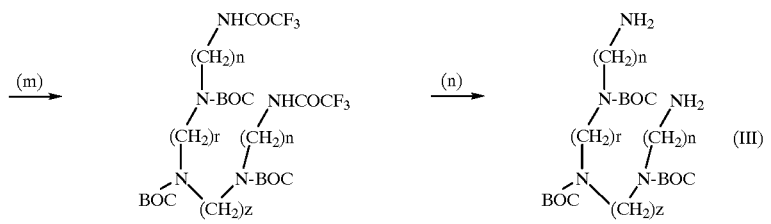

What is claimed is:

1. A bis-platinum(II) complex comprising formula (I):

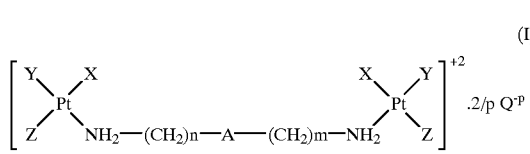

wherein two of the X,Y, and Z ligands attached to each platinum atom are ammonia and the other ligand is selected from the group consisting of chloride, bromide, iodide, and a ($C_1$–$C_4$)acyloxy group;

n and m are each independently an integer of two to eight;

p is one or two;

A is selected in the group consisting of —B—, —B—($CH_2$)$_r$—B—, —B—($CH_2$)$_r$—B—($CH_2$)$_z$—B—, wherein r and z are an integer ranging of two to eight, B is a group —$NR^1$— or —$N(R^2)^+$ $1/pQ^{-p}$, which $R^1$ is selected from the group consisting of hydrogen, ($C_1$–$C_4$)alkyl, ($C_1$–$C_4$)acyl, tert-butyloxycarbonyl, and $R^2$ is selected in the group consisting of hydrogen, ($C_1$–$C_4$)alkyl; and $Q^{-p}$ is an anion selected from chloride, bromide, iodide, nitrate, sulfate, hydrogensulfate, perchlorate.

2. The complex of claim 1, wherein the $NH_2$-($CH_2$)$_n$-A-($CH_2$)$_m$-$NH_2$ is a spermine.

3. The complex of claim 1, wherein the $NH_2$-($CH_2$)$_n$-A-($CH_2$)$_m$-$NH_2$ is a spermidine.

4. The complex of claim 1, wherein X and Z are ammonia and attached to each platinum atom in the trans position.

5. The complex of claim 1, wherein the non-ammonia ligand is a chloride group.

6. A method of preparing the bis-platinum(II) complex of claim 1, comprising the steps of reacting a precursor of formula [Pt(X)(Y)(Z)Cl] with diimethylformamide in the presence of an equimolar amount of $AgNO_3$, at a temperature of 0° C. to 50° C., to produce the activated intermediate of formula (II):

[Pt(X)(Y)(Z)(DMF)]$^+$$NO_3^-$ (II);

condensing two moles of intermediate (II) with a polyamine of formula (III):

at a temperature of about –40° C. to about room temperature wherein A' is selected from the group consisting of—B'—, —B'—($CH_2$)$_r$—B'—, and —B'—($CH_2$)$_r$—B'—($CH_2$)$_z$—B'—, wherein B' is a group —$NR^1$ or $N(R^2)_2^+$ $1/pQ^{-p}$, wherein $R^1$ is selected from the group consisting of ($C_1$–$C_4$) alkyl, ($C_1$–$C_4$)acyl, and tert-butyloxycarbonyl, and $R^2$ is a ($C_1$–$C_4$)alkyl, to produce a platinum complex of formula (I'):

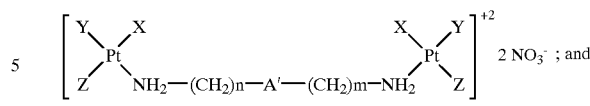

separating by chromatography any diastereomers formed.

7. The method of claim 6, wherein B' has a protecting group suitable for a secondary amine, and B' is a group which can be converted into A by removing the protecting group from the formula (I') following the condensing step.

8. The method of claim 7, wherein the protecting group is a tert-butyloxycarbonyl group.

9. The method of claim 6, further comprising the step of neutralizing the compounds of formula (I) at a temperature of about –10° C. to about room temperature, by treatment with a suitable base in a stoichiometric amount to produce compounds of formula (I) in which B is —NH— or a —N($C_1$–$C_4$)alkyl.

10. The method of claim 9, wherein the suitable base is a non-aqueous solution of a hydroxide of an alkali or alkaline-earth metal.

11. The method of claim 6, wherein the reaction of the precursor is performed at about room temperature.

12. The method of claim 6, wherein the condensing is performed at a temperature of about –20° C.

13. A method of treating tumors in a mammal comprising the step of administering to the mammal a tumor regressive about of at least one bis-platinum(II) complex of claim 1.

14. The method of claim 13, wherein the bis-platinum(II) complex is administered with at least one agent which enhances antitumor activity.

15. The method of claim 13, wherein the bis-platinum(II) complex is administered with at least one agent which reduces any undesirable side effects associated with the bis-platinum(II) complex treatment.

16. The method of claim 13, wherein the tumor regressive amount is between 0.1 and 1200 mg/kg weight of the mammal.

17. The method of claim 13, wherein the bis-platinum(II) complex is administered with at least one other bis-platinum(II) complex which is tumor regressive.

18. The method of claim 13, wherein the bis-platinum(II) complex is administered as a sterile aqueous solution.

19. The method of claim 18, wherein the sterile aqueous solution has a concentration of between 0.1 and 0.9 mg/ml of sodium chloride.

20. The method of claim 12, wherein the bis-platinum(II) complex is administered orally.

21. A pharmaceutical composition for the treatment of tumors in mammals comprising an anti-tumor effective amount of a bis platinum(II) complex of claim 1 and a pharmaceutically acceptable carrier.

* * * * *